United States Patent [19]
Drent et al.

[11] Patent Number: 4,939,307
[45] Date of Patent: Jul. 3, 1990

[54] PROCESS FOR HYDROGENATION OF ESTERS INTO ALCOHOLS

[75] Inventors: Eit Drent; Willem W. Jager, both of Amsterdam, Netherlands

[73] Assignee: Shell Oil Company, Houston, Tex.

[21] Appl. No.: 313,918

[22] Filed: Feb. 23, 1989

[30] Foreign Application Priority Data

Mar. 4, 1988 [GB] United Kingdom ............... 8805264

[51] Int. Cl.$^5$ ................ C07C 27/04; C07C 29/132
[52] U.S. Cl. ......................... 568/864; 568/814; 568/861
[58] Field of Search ............... 568/814, 868, 864, 861

[56] References Cited

U.S. PATENT DOCUMENTS

| | | | |
|---|---|---|---|
| 4,041,083 | 8/1977 | Gradeff et al. | 260/617 C |
| 4,346,240 | 8/1982 | Grey et al. | 568/842 |
| 4,611,085 | 9/1986 | Kitson | 568/885 |
| 4,614,749 | 9/1986 | Sapienza et al. | 518/700 |
| 4,628,130 | 12/1986 | Bournonville et al. | 568/885 |

*Primary Examiner*—Werren B. Lone

[57] ABSTRACT

A process for hydrogenation of esters of the formula:

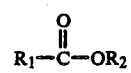

(I)

or

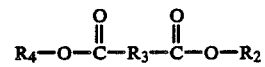

(II)

wherein $R_1$ represents hydrogen or a hydrocarbyl group, wherein $R_2$ and $R_4$ represent a hydrocarbyl group, and wherein $R_3$ represents a hydrocarbylene group, which process comprises contacting said ester with hydrogen and carbon monoxide in the presence of a catalyst system which comprises:
(a) a compound containing a cation of an element selected from Group VIII of the Periodic Table of the Elements,
(b) an alcoholate of an alkali metal and/or alkaline earth metal, and
(c) an alcohol.

19 Claims, No Drawings

PROCESS FOR HYDROGENATION OF ESTERS INTO ALCOHOLS

FIELD OF THE INVENTION

The invention relates to a process for the hydrogenation of esters and more particularly to a process for the hydrogenation of esters into alcohols with a hydrogen containing gas and in the presence of a catalyst system.

BACKGROUND OF THE INVENTION

Such processes are in general known from a great variety of literature and are using a large number of diverging types of catalysts. However, these conventional industrial scale catalytic hydrogenation processes have the disadvantage that they are using rather pure hydrogen at high pressures such as disclosed in e.g. U.S. Pat. Nos. 4,628,130 and 4,346,240 and German Pat. No. 1,768,262, and/or high temperatures or that they are using catalyst systems, which can only be removed from the desired product by laborious methods, which inevitably cause significant additional costs.

It will be appreciated that there is still a growing need for an economically attractive process for hydrogenation of esters into alcohols, which should not inevitably require the use of rather pure hydrogen gas, but should be carried out in the presence of cheaper hydrogen containing gas such as synthesis gas or other commercially available hydrogen containing gas mixtures, and should use simpler and therefore cheaper catalyst systems.

Therefore, it is an object of the present invention to provide such an improved process.

SUMMARY OF THE INVENTION

This invention relates to a process for the hydrogenation of esters of the formula:

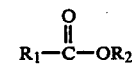

(I)

or

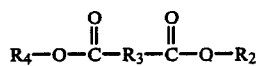

(II)

wherein $R_1$ represents hydrogen or a hydrocarbyl group, $R_2$ and $R_4$ represent a hydrocarbyl group, and wherein $R_3$ represents a hydrocarbylene group, which comprises contacting said esters with hydrogen and carbon monoxide and a catalyst system which comprises:
(a) a compound containing a cation of an element selected from Group VIII of the Periodic Table of the Elements,
(b) an alcoholate of an alkali metal and/or alkaline earth metal, and
(c) an alcohol.

DESCRIPTION OF THE PREFERRED EMBODIMENTS

Preferably esters are hydrogenated, wherein $R_1$ represents an alkyl or alkenyl group containing 1-20 carbon atoms and more preferably about 3 to about 12 carbon atoms, an aryl group or aralkyl group containing 1 to about 6 carbon atoms in the alkyl residue, with the aryl preferably being phenyl and the aralkyl preferably being benzyl, wherein $R_2$ and $R_4$ are hydrocarbyl groups as specified hereinbefore for $R_1$ and are the same or different in one molecule, and wherein $R_3$ represents an alkylene group or an alkenylene group of 1 to about 10 carbon atoms or an arylene group, and more preferably phenylene or naphthylene.

As component (a), several salts of elements of Group VIII of the Periodic Table of the Elements may be used, and preferably salts of palladium, cobalt or nickel. Most preferred are nickel salts. The anion of the salt in component (a) may be derived from a great variety of acids and preferably from carboxylic acids or hydrochloric acid, sulfuric acid, nitric acid, phosphoric acid, or sulfonic acids.

Among these acids, preference is given to alkanoic acids having 1 to about 10 carbon atoms in the chain such as formic acid, acetic acid, propionic acid, butanoic acid, 2-methylpropanoic acid, pentanoic acid, 3-methylbutanoic acid, 2,2-dimethylpropanoic acid, hexanoic acid, heptanoic acid and octanoic acid, oxalic acid or to paratoluene sulfonic acid. More preferably, the acid is formic acid, acetic acid or oxalic acid.

Most preferably nickel formate, nickel acetate, nickel oxalate or nickel tosylate are used.

The anions of component (a) may also be derived from dicarboxylic acids such as malonic acid, dimethyl malonic acid, succinic acid, glutaric acid, adipic acid, pimelic acid, suberic acid, azelaic acid, phthalic acid, isophthalic acid and terephthalic acid.

The carboxylic acids from which the anion of component (a) may be derived may contain substituents, for example alkoxy groups, particularly those having not more than five carbon atoms, hydroxy groups, cyano groups and fluorine, chlorine, bromine and iodine atoms.

Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5-dichlorobenzoic acid, 3,5-dibromobenzoic acid, cyano acetic acid, monofluoro acetic acid, difluoroacetic acid, trifluoroacetic acid and trichloroacetic acid.

A mixture of the salts may also be used in component (a) e.g. of a formate and an oxalate of a formate and an acetate, or of an acetate and an oxalate.

The salts to be used as component (a) may contain crystal water, but are preferably free therefrom.

The alcoholate to be used as component (b) is preferably a sodium alcoholate or a potassium alcoholate. Among the alcoholates preference is given to alkoxides, particularly to those having from 1 to 20 carbon atoms per molecule, such as sodium methoxide, sodium ethoxide, sodium propoxide, sodium butoxide, sodium isobutoxide, sodium tert-pentoxide and potassium 2-methyldodec-2-oxide.

Component (b) may also consist of a mixture of alcoholates, e.g. potassium tertiary butoxide and potassium tertiary pentoxide or sodium tertiary butoxide and sodium tertiary pentoxide.

The alcohol of component (c) may be cycloaliphatic or aliphatic, but is preferably aliphatic. Preference is given to alkanols, in particular to those having in the range of from 1 to 20 carbon atoms per molecule. Among the latter alkanols those having in the range of from 4 to 20 carbon atoms per molecule are preferred. Tertiary alcohols are more preferred. Examples of suitable alkanols are t-butyl alcohol, t-pentyl alcohol, hexanol, heptanol and alkanols with from 8 to 20 carbon atoms per molecule. Tertiary butyl alcohol and tertiary pentyl alcohol are particularly preferred.

Polyhydric alcohols may also be used, for example ethylene glycol, propylene glycol, 1,3-dihydroxypropane, 1,2-butanediol, 1,3-butanediol, 1,4-butanediol, 2,3-butanediol, 1,2-pentanediol or glycerol.

Component (b) may be a mixture of alcohols, for example of tertiary butyl alcohol and ethylene glycol or of tertiary phenyl alcohol and 1,4-butanediol.

The process of the present invention is preferably used for hydrogenation of esters according to formula I wherein $R_1$ represents aryl and more preferably phenyl or naphthyl and wherein $R_2$ represents an alkyl residue or aralkyl residue and preferably methyl, ethyl or benzyl, wherein $R_3$ represents phenylene, naphthylene or alkylene or alkenylene having 1–4 carbon atoms, and wherein $R_4$ represents an alkyl residue or aralkyl residue. More particularly, the hydrogenation process of the present invention is used for the conversion of alkanoic acid esters or, aromatic esters such as lower alkyl propionate, lower alkyl benzoate, lower alkyl phenylacetate, lower alkyl naphthoate, di(lower alkyl)terephthalate, di(lower alkyl)phthalate, di(lower alkyl)isophthalate.

More preferably methyl propionate, methyl undecenoate, methyl benzoate, ethylbenzoate, di(methyl)phthalate, di(methyl)isophthalate, di(methyl)terephthalate, di(ethyl)phthalate, di(ethyl)isophthalate or di(ethyl)terephthalate are hydrogenated according to the present process.

The activation of the catalyst system, providing the most attractive results, may be reached by keeping the mixed components under an atmosphere of nitrogen or any other suitable inert gas during 0.3 to 1 hour at a temperature in the range of from 20°–60° C. and more preferably 35°–50° C.

The process according to the present invention may be carried out at a temperature and a pressure which are not critical and may vary within wide ranges. Preferably, a temperature in the range of from about 30° C. to 150° C. and a pressure in the range of from 5 to 100 bar are used.

The process according to the present invention may be carried out with an organic diluent in which the catalytic system is dissolved or suspended. Suitably, a weight ratio of organic diluent to component (a) in the range of from about 0.1 to about 5000 is used, but this weight ratio may be lower than about 0.1 or higher than about 5000.

Any inert diluent may in principle be used. Examples of suitable diluents are ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; sulfones, such as diisopropyl sulfone, tetrahydrothiophene 1,1-dioxide (also referred to as "sulfolane"), 2-methyl-4-butylsulfolane and 3-methylsulfolane. Mixtures of two or more solvents may be used. Very good results have been obtained with ethers and the use of diglyme is most preferred.

The process according to the present invention is preferably carried out using a molar ratio of the starting ester to component (a) in the range of from about 0.5:1 to about 100:1 and, more preferably, from about 1:1 to about 50:1, but the use of molar ratios below 0.5 and above 100 is not excluded. The process may be carried out using a molar ratio of component (a) to component (b) which is not critical and may vary within wide ranges, preferably in the range of from about 10:1 to about 1:100.

The carbon monoxide and hydrogen may be used as pure gases or diluted with an inert gas such as an inert gas or nitrogen. The process according to the present invention may be suitably carried out using a molar ratio carbon monoxide to hydrogen in the gaseous mixture in the range of from about 0.05 to about 0.3. The carbon monoxide and hydrogen may be obtained by partial oxidation or steam reforming of hydrocarbons, for example of natural gas.

It is true, that catalyst systems containing the presently proposed components are known from e.g. U.S. Pat. No. 4,614,749 and Japanese Patent Application No. 56.169,634.

However, on the one hand in U.S. Pat. No. 4,614,749 such catalyst systems are only used for the preparation of methanol from syngas, whereas as additional components an alkali metal hydride and a carbonyl complex of one of the Group VI metals are used. On the other hand the Japanese Patent Application No. 56,169,634 also discloses a process for the preparation of methanol from syngas mixtures using a catalyst, comprising a nickel compound being not derived from the before-mentioned carboxylic acids, and an alkali metal alkoxide while moreover according to the examples 10–12 also alkali metal hydrides were included in these catalysts.

It will therefore be appreciated that a person skilled in the art could not find any teaching in these publications to come to the present process and that the attractive results obtained according to the process of the present invention using mixtures of hydrogen and carbon monoxide can only be regarded as surprising by such skilled person.

According to a specific embodiment of the process of the present invention methylpropionate, methyl benzoate, or methyl undecenoate is hydrogenated into methanol, and propanol; methanol and benzylalcohol and methanol and 1-undecenol respectively, at 80°–120 ° C. and a total pressure of 30–50 bar, during a total reaction period of from 3–5 hours, showing attractive conversions.

The following examples further illustrate the invention without however restricting the scope thereof to these particular embodiments. All experiments were carried out in a 300 ml magnetically stirred Hastelloy C (Registered Trade Mark) autoclave. The reaction mixtures obtained were analyzed by means of gas-liquid chromatography.

EXAMPLE 1

The autoclave is initially charged with 50 ml diglyme, 10 mmol nickel(II)formate and 20 mmol tert-.amylalcohol.

The catalyst system was activated during 0.5 hour at 45° C. under nitrogen.

Thereafter 50 ml tertiary amylalcohol, 60 mmol potassium tertiary butylate and 20 ml methyl propionate were added. Carbon monoxide is added to a partial pressure of 5 bar, where hydrogen is added to a partial pressure of 30 bar at ambient temperature.

The reaction mixture was then heated up to 80° C. and kept at this temperature during 5 hours, whereas after 15 min hydrogen was added until a pressure increase of 35 bar and after 45 min carbon monoxide was added until a pressure increase of 5 bar and hydrogen was added until a partial pressure increase of 10 bar.

After termination of the reaction, the mixture was allowed to cool to room temperature and analyzed.

3.3 g methanol and 2.6 g propanol were found.

EXAMPLE 2

The autoclave is initially charged with 50 ml diglyme, 10 mmol nickel(II)formate and 20 mmol tertiary amylalcohol.

The catalyst system was kept during 0.5 hour at 45° C. under nitrogen.

Thereafter 10 ml tert.amylalcohol in 40 ml diglyme, 60 mmol potassium tertiary butylate and 10 ml methylpropionate were added. Carbon monoxide is added to a partial pressure of 5 bar while hydrogen is added to a partial pressure of 30 bar, whereafter the temperature was increased from 45° C. to 100° C. The reaction mixture was kept at a temperature of 100° C. during 5 hours. After 10 min hydrogen was added until a pressure increase of 30 bar was reached.

After termination of the reaction the mixture was allowed to cool to room temperature and analyzed. 2.5 g methanol and 2.5 g propanol were found.

EXAMPLE 3

In about the same way as described under Example 2, an experiment was carried out, with the difference being that the autoclave was kept at 120° C. for 3 hours, giving 3.2 g methanol and 3.5 g propanol.

EXAMPLE 4

In the same way as described under Example 2, an experiment was carried out, with the difference being that carbon monoxide was added to a partial pressure of 2 bar instead of 5 bar, whereas the autoclave was kept at 120° C. for 5 hours, giving a yield of 2.0 g methanol and 3.1 g propanol.

EXAMPLE 5

In the same way as described under Example 2, an experiment was carried out with the difference being that 10 ml methylbenzoate was included in the autoclave instead of 10 ml methyl propionate. The partial hydrogen pressure was 30 bar, while the autoclave was kept at 120° C. for 5 hours, giving a yield of 2.5 g methanol and 7.5 g benzylalcohol.

EXAMPLE 6

In about the same way as described under Example 2, an experiment was carried out with difference being that 10 ml methyl-undecenoate was included in the autoclave instead of 10 ml methylpropionate, while after 5 min hydrogen was added until a pressure increase of 30 bar was reached. The autoclave was kept at 80° C. for 5 hours giving a yield of 2.4 g methanol and about 1 g 1-undecenol.

We claim:

1. A process for the hydrogenation of esters into alcohols, which process comprises contacting esters of the formula:

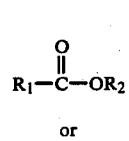

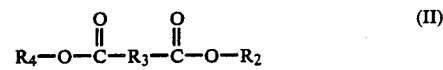

wherein $R_1$ represents hydrogen or a hydrocarbyl group having 1 to about 20 carbon atoms, $R_2$ and $R_4$ represent a hydrocarbyl group having 1 to about 20 carbon atoms, and wherein $R_3$ represents a hydrocarbylene group having 1 to about 10 carbon atoms, with hydrogen and carbon monoxide at a temperature in the range of from about 30° C. to about 150° C. and a pressure in the range of from about 5 bar to about 100 bar in the presence of a catalyst system comprising:
   (a) a compound containing a cation of an element selected from Group VIII of the Periodic Table of the Elements,
   (b) an alcoholate of an alkali metal and/or alkaline earth metal, and
   (c) an alcohol.

2. The process of claim 1, wherein $R_1$ represents an alkyl or alkenyl group containing 1 to about 20 carbon atoms, an aryl group or aralkyl group, containing 1 to about 6 carbon atoms in the alkyl residue, wherein $R_2$ and $R_4$ are hydrocarbyl groups as specified hereinbefore for $R_1$ and are the same or different in one molecule, and wherein $R_3$ represents an alkylene group or an alkenylene group of 1 to about 10 carbon atoms or an arylene group.

3. The process of claim 2 wherein $R_1$ represents an alkyl or alkenyl group containing about 3 to about 12 carbon atoms, a phenyl group or benzyl group, and wherein $R_3$ represents a phenylene group.

4. The process of claim 1 wherein component (a) is selected from a palladium, cobalt or nickel salt.

5. The process of claim 4 wherein component (a) is a nickel salt.

6. The process of claim 5 wherein said nickel salt is selected from nickel formate, nickel acetate, nickel oxalate and nickel tosylate.

7. The process of claim 1 wherein component (b) is selected from sodium alcoholate and potassium alcoholate.

8. The process of claim 7 wherein component (b) is selected from sodium methoxide, sodium ethoxide, sodium propoxide, sodium butoxide, sodium isobutoxide, sodium tertiary pentoxide and potassium 2-methyldodec-2-oxide.

9. The process of claim 1 wherein component (c) is an alkanol having from about 4 to about 20 carbon atoms.

10. The process of claim 9 wherein component (c) is selected from tertiary butyl alcohol and tertiary pentyl alcohol.

11. The process of claim 1 wherein said process is carried out in the presence of an organic diluent.

12. The process of claim 11 wherein a weight ratio of organic diluent to component (a) in the range of from about 0.1 to about 5000 is used.

13. The process of claim 1 wherein a molar ratio of starting ester to component (a) in the range of from about 0.5:1 to about 100:1 is used.

14. The process of claim 13 wherein said molar ratio is in the range of from about 1:1 to about 50:1.

15. The process of claim 1 wherein a molar ratio of component (a) to component (b) in the range of from about 0.1:1 to about 100:1 is used.

16. The process of claim 11 wherein said diluent is an ether.

17. The process of claim 16 wherein said diluent is diglyme.

18. The process of claim 1 wherein a molar ratio of carbon monoxide to hydrogen in the range of from about 0.05 to about 0.3 is used.

19. The process as of claim 1 wherein said ester which is hydrogeneated is selected from methylpropionate, methyl benzoate, and methyl undecenoate.

* * * * *